(12) United States Patent
Krueger et al.

(10) Patent No.: US 9,896,428 B2
(45) Date of Patent: Feb. 20, 2018

(54) PROCESS FOR PREPARING CHLOROACETALDEHYDE ACETALS

(71) Applicant: Wacker Chemie AG, Munich (DE)

(72) Inventors: Benno Krueger, Burgkirchen (DE); Wolfgang Doering, Mehring (DE); Gerald Fleischmann, Bergausen (DE); Hermann Petersen, Berghausen (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 15/066,090

(22) Filed: Mar. 10, 2016

(65) Prior Publication Data

US 2016/0272610 A1 Sep. 22, 2016

(30) Foreign Application Priority Data

Mar. 18, 2015 (DE) .................. 10 2015 204 901

(51) Int. Cl.
| | |
|---|---|
| *C07D 321/06* | (2006.01) |
| *C07C 41/09* | (2006.01) |
| *C07D 319/06* | (2006.01) |
| *C07C 41/56* | (2006.01) |

(52) U.S. Cl.
CPC ............ *C07D 321/06* (2013.01); *C07C 41/09* (2013.01); *C07C 41/56* (2013.01); *C07D 319/06* (2013.01)

(58) Field of Classification Search
None
See application file for complete search history.

(56) References Cited

U.S. PATENT DOCUMENTS 4,440,959 A 4/1984 Deinhammer

FOREIGN PATENT DOCUMENTS

| DE | 1235880 B | 3/1967 |
| EP | 0368613 B1 | 5/1990 |
| EP | 0456157 B1 | 11/1991 |

OTHER PUBLICATIONS

Gelas et al., "Cyclic acetals. XI. 2-Hydroxyalkyl- and 5-hydroxymethyl-1,3-dioxanes. Intramolecular hydrogen bonding. Heterobicyclization reactions." Ec. Natl. Super. Chim., Univ. Clermont-Ferrand, Clermont-Ferrand, Fr., Bulletin de la Societe Chimique de France (1972), (9), 3471-3479.
English language abstract for Gelas et al., "Cyclic acetals. XI. 2-Hydroxyalkyl- and 5-hydroxymethyl-1,3-dioxanes. Intramolecular hydrogen bonding. Heterobicyclization reactions." Ec. Natl. Chim. Univ. Clermont-Ferrand, Clermont-Ferrand, Fr., Bulletin de la Societe Chimique de France (1972), (9), 3471-3479, Dec. 26, 2016.
Liang et al., "Novel carbon-based strong acid catalyst from starch and its catalytic activities for acetalization", J Mater Sci, 46:5345-5349 (2011).
Meskens, "Methods for the Preparation of Acetals from Alcohols or Oxiranes and Carbonyl Compounds", Synthesis 1981(07):501-522 (1980), Dec. 26, 2016.

*Primary Examiner* — Rosalynd A Keys
(74) *Attorney, Agent, or Firm* — Caesar Rivise, PC

(57) ABSTRACT

The invention relates to a process for preparing chloroacetaldehyde acetals of monohydric, dihydric or higher-functionality aliphatic alcohols, in which the chloroacetaldehyde acetal is obtained from an aqueous chloroacetaldehyde solution in the presence of the alcohol to be acetalized and an acid catalyst by azeotropic removal of water with the aid of a solvent, wherein the solvent is a halogenated solvent.

6 Claims, No Drawings

PROCESS FOR PREPARING CHLOROACETALDEHYDE ACETALS

BACKGROUND OF THE INVENTION

The invention relates to a process for preparing acyclic and cyclic chloroacetaldehyde acetals from aqueous chloroacetaldehyde solutions by azeotropic removal of water with the aid of a suitable solvent.

It is known that chloroacetaldehyde acetals can be prepared by chlorination of vinyl compounds (vinyl acetate, vinyl chloride, vinyl ethers) in alcoholic media. A discussion of this prior art may be found in U.S. Pat. No. 4,440,959.

EP0456157B1 describes the preparation of chloroacetaldehyde acetals from the trimer of chloroacetaldehyde in good quality and yield. The trimer of chloroacetaldehyde used for the preparation is described in EP0368613B1. This process for preparing the required trimer of chloroacetaldehyde is very complicated, requires large amounts of solvent and concentrated sulfuric acid and gives a poor yield (about 50%), so that this process is not industrially relevant.

It is also known that acetals can be prepared by means of the Fischer acetalization process, i.e. direct reaction of the aldehyde with alcohols in the presence of an acid catalyst and removal of the water of reaction by means of azeotropic distillation (Meskens, Synthesis 501-522 (1981)), but this process is meaningless for low-boiling aldehydes since the removal of water is incomplete or does not occur and desiccants (e.g. calcium chloride, etc.) therefore have to be added. The production process from 80% strength chloroacetaldehyde and alcohols as described in DE1235880B, in which the removal of water occurs exclusively by means of water-binding agents, is similar. However, these water-binding agents not only make the preparation expensive but also form a considerable amount of waste which in the case of the chlorinated aldehydes is difficult to dispose of because of the content of chlorinated constituents. In addition, 80% strength chloroacetaldehyde is difficult to prepare and also not readily handleable because of the decomposition potential.

Xuezheng Liang, Chunqing Li, Chenze Qi, J. Mater Sci (2011) 46:5345-5349, describe, inter alia, the preparation of cyclic chloroacetaldehyde acetals from chloroacetaldehyde and the corresponding diols in yields of 99% by azeotropic distillation with the aid of cyclohexane in a Dean-Stark apparatus. However, there is no indication of the form in which chloroacetaldehyde is used and the maximum batch size described is only 0.1 mol of chloroacetaldehyde and only 10 ml of cyclohexane as water entrainer. On the basis of our own knowledge, cyclohexane is unsuitable for azeotropic acetalization of chloroacetaldehyde since it readily removes chloroacetaldehyde from the reaction mixture (cf. comparative example 3).

Chloroacetaldehyde is readily available in high purity in aqueous solution (up to 45% chloroacetaldehyde). However, there is no known industrially relevant process which is suitable for preparing chloroacetaldehyde acetals from aqueous chloroacetaldehyde solutions. Only processes which start out from chloroacetaldehyde hemihydrate, which is difficult to prepare and owing to the possibility of decomposition is dangerous to handle, are known.

DESCRIPTION OF THE INVENTION

It is an object of the invention to provide a process for preparing chloroacetaldehyde acetals of monohydric, dihydric or higher-functionality aliphatic alcohols from chloroacetaldehyde.

The object is achieved by a process in which the chloroacetaldehyde acetal is obtained from an aqueous chloroacetaldehyde solution in the presence of the alcohol to be acetalized and an acid catalyst by azeotropic removal of water with the aid of a solvent, wherein the solvent is a halogenated solvent.

In the case of higher-functionality alcohols, which for the purposes of the present invention are preferably 3- to 5-hydric alcohols, free hydroxyl groups can remain in the chloroacetaldehyde acetal or two or more chloroacetaldehyde acetal groups can be formed in the molecule.

The halogenated solvent is preferably a monohalogenated or multiply halogenated, particularly preferably chlorinated or fluorinated, hydrocarbon which has from 1 to 5 carbon atoms and forms azeotropes having boiling points in the range from 25° C. to 80° C. with water under atmospheric pressure (101.3 kPa). For the purposes of the present invention, multiply halogenated hydrocarbons are preferably dihalogenated to tetrahalogenated hydrocarbons.

The halogenated solvent is particularly preferably trichloromethane.

The aqueous chloroacetaldehyde solution is preferably an aqueous solution containing from 5% to 70% by weight, preferably from 30% to 50% by weight, of chloroacetaldehyde. Such solutions are readily available in high purity.

The alcohol to be acetalized is preferably a monohydric, dihydric or higher-functionality aliphatic alcohol having from one to twelve carbon atoms; it is particularly preferably a monohydric or dihydric aliphatic alcohol having from one to twelve carbon atoms.

The monohydric aliphatic alcohols having from one to twelve carbon atoms can be saturated or unsaturated and contain aromatic groups or substituents which are stable under the reaction conditions (e.g. ethers).

The dihydric aliphatic alcohols having from one to twelve carbon atoms can be saturated or unsaturated and contain aromatic groups or substituents which are stable under the reaction conditions, e.g. ethers. The hydroxy groups can be in the alpha, beta or gamma position relative to one another.

The higher-functionality aliphatic alcohols having from one to twelve carbon atoms can be saturated or unsaturated and contain aromatic groups or substituents which are stable under the reaction conditions (e.g. ethers).

The monohydric aliphatic alcohol is preferably methanol, ethanol, n-propanol, i-propanol, 1-butanol, 2-butanol, isobutanol, tert-butanol, 1-pentanol, cyclohexanol, cyclopentanol.

The dihydric aliphatic alcohol is preferably 1,2-ethanediol, 1,2-propanediol, 1,3-propanediol, 1,4-butanediol, 2,3-butanediol, 1,3-hexanediol, cis-1,3-cyclohexanediol, cis-1,2-cyclohexanediol.

The higher-functionality aliphatic alcohol is preferably glycerol, pentaerythritol, xylitol.

The acid catalyst is preferably an inorganic or organic acid, e.g. hydrochloric acid, sulfuric acid, phosphoric acid, methanesulfonic acid, toluenesulfonic acid, trifluoromethane-sulfonic acid, trifluoroacetic acid, benzenephosphonic acid, or a strong acid ion exchange resin. For the purposes of the present invention, a strong acid ion exchange resin is preferably an ion exchange resin having sulfonic acid groups. Such strong acid ion exchange resins are commercially available under the trade name Dowex® or Amberlite®.

Particular preference is given to phosphoric acid, toluenesulfonic acid, sulfuric acid or Dowex®.

The chloroacetaldehyde acetal is preferably an acyclic or cyclic chloroacetaldehyde acetal having from one to twelve carbon atoms.

The solvent is preferably present in the reaction mixture in a volume ratio of solvent to chloroacetaldehyde solution of from 1:10 to 5:1.

The acid catalyst is preferably used in an amount of from 0.01 mol % to 2 mol % based on the chloroacetaldehyde used. Owing to the acidic pH of the chloroacetaldehyde solution, a reaction without catalyst is also possible, but the reaction rate is then too slow for an industrial process.

Chloroacetaldehyde acetals can surprisingly be obtained in high yield at high purity in a simple manner by dewatering aqueous chloroacetaldehyde solutions by means of a halogenated solvent in the presence of the alcohol to be acetalized and an acid catalyst. This is possible even in the case of low-boiling alcohols. In the case of acid-sensitive chloroacetaldehyde acetals, the acid catalyst has to be neutralized before the distillation. This is preferably effected by means of amines whose boiling point is significantly higher than the boiling point of the product. It is also possible to use alkali metal or alkaline earth metal carbonates, hydrogencarbonates or oxides.

The use of aliphatic hydrocarbons such as hexane, pentane, cyclohexane as solvents has been found to be unsuitable since in this case large amounts of chloroacetaldehyde are discharged in the water separator and the yield of chloroacetaldehyde acetal is therefore drastically reduced. Particularly in the case of low-boiling alcohols, which for the purposes of the present invention are preferably alcohols having a boiling point in the range from 65° C. to 80° C. under standard conditions, it has been found to be advantageous for the solvent used as entrainer to remove only small amounts of the alcohol, which for the purposes of the present invention are preferably amounts of less than 20% by weight, from the reaction mixture. Experiments in relation to the present invention have surprisingly indicated that monohalogenated or multiply halogenated hydrocarbons which have from one to five carbon atoms and form an azeotrope having a boiling point in the range from 25° C. to 80° C. with water under atmospheric pressure are preferred for use as solvent. Trichloromethane has been found to be particularly useful. Owing to interactions between chlorinated molecules, this removes chloroacetaldehyde from the reaction mixture to a considerably smaller extent.

An advantage of the process of the invention is that the solvent or, in the case of lower alcohols such as methanol, ethanol or isopropanol, the mixture of solvent and the corresponding alcohol, which is used for the removal of water can be used again without further purification in the process of the invention. A further advantage is that, apart from small amounts of distillation residue, hardly any waste is obtained (e.g. in examples 1 and 6, <2% of the amount used).

The following examples serve to illustrate the invention.

Example 1: Preparation of
2-chloromethyl-1,3-dioxepane 1744.4 g of 45% strength aqueous chloroacetaldehyde solution (10 mol of chloroacetaldehyde), 919.0 g (10.2 mol) of 1,4-butanediol, 1 l of trichloromethane and 2 g of p-toluenesulfonic acid were placed in a 4 l four-neck flask provided with water separator, reflux condenser, precision glass stirrer and internal thermometer. The two-phase mixture was heated under reflux on the water separator while stirring until no more water separates out (about 10 hours). The reaction mixture here became a single phase. The reaction mixture was then distilled under reduced pressure (15 mbar, 80° C.)

Yield: 1459.3 g (96.9%), purity >99% (GC)

Comparative Example 1

The experiment was carried out as described in example 1, except that n-hexane was used instead of trichloromethane.

Yield 873.5 g (58%), purity >99% (GC)

Example 2: Preparation of Chloroacetaldehyde
Diethyl Acetal 2442 g of 45% strength aqueous chloroacetaldehyde solution (14 mol of chloroacetaldehyde), 1612 g (35 mol) of ethanol, 1500 ml of trichloromethane and 2.8 g of p-toluenesulfonic acid were placed in a 6 l four-neck flask provided with water separator, reflux condenser, packed column, precision glass stirrer and internal thermometer and metering unit. The two-phase mixture was heated under reflux on the water separator while stirring until no more water separates out (7 hours). The reaction mixture here becomes a single phase. A further 322.5 g (7 mol) of ethanol were then introduced under reflux and with separation of water. Another 253.7 g (4.35 mol) of ethanol and also 500 g of trichloromethane were subsequently added and the mixture was heated under reflux on the water separator until no more water separated out. 31.2 g of tributylamine are subsequently added to effect neutralization and the reaction mixture is fractionally distilled under reduced pressure (100 mbar, 90° C.)

Yield 1987 g (93.0% of theory) purity >99% (GC)

Example 3: Preparation of
2-chloromethyl-1,3-dioxolane 174.44 g of 45% strength aqueous chloroacetaldehyde solution (1 mol of chloroacetaldehyde), 68.28 g (1.1 mol) of ethylene glycol, 200 ml of trichloromethane and 0.2 g of p-toluenesulfonic acid were placed in a 1 l four-neck flask provided with water separator, reflux condenser, precision glass stirrer and internal thermometer and metering unit. The two-phase mixture was heated under reflux on the water separator while stirring until no more water separates out (total of about 7 hours). The reaction mixture here becomes a single phase. 2.2 g of tributylamine are then added to neutralize the p-toluenesulfonic acid and the reaction mixture is distilled under reduced pressure (75 mbar, 85° C.)

Yield 111.6 g (91%), purity >99% (GC)

Example 4: Preparation of Chloroacetaldehyde
Dimethyl Acetal 174.44 g of 45% strength aqueous chloroacetaldehyde solution (1 mol of chloroacetaldehyde), 16.02 g (0.5 mol) of methanol, 200 ml of trichloromethane and 0.2 g of p-toluenesulfonic acid were placed in a 1 l four-neck flask provided with water separator, reflux condenser, precision glass stirrer and internal thermometer and metering unit. The two-phase mixture was heated under reflux on the water separator while stirring until no more water separates out. A further 48 g (1.5 mol) of methanol were subsequently introduced under reflux and with separation of water (total of about 7 hours). The reaction mixture here becomes a single phase. 2.2 g of tributylamine are then added to neutralize the p-toluenesulfonic acid and the reaction mixture is distilled under reduced pressure (100 mbar, 90° C.)

Yield 99.7 g (80%), purity >99% (GC)

Comparative Example 2

The experiment was carried out as described in example 4, except that n-hexane was used instead of trichloromethane. The experiment was stopped after 4 hours since a large part of the methanol and chloroacetaldehyde had been carried out from the reaction mixture into the aqueous phase in the water separator.

Comparative Example 3

The experiment was carried out as described in example 4, except that cyclohexane was used instead of trichloromethane. The experiment was stopped after 4 hours since a large part of the methanol and chloroacetaldehyde had been carried out from the reaction mixture into the aqueous phase in the water separator.

Example 5: Preparation of Chloroacetaldehyde Dimethyl Acetal

The experiment was carried out as described in example 4, except that 4 mol of methanol (1.5 mol initially charged and 2.5 mol metered in) were used instead of 2 mol of methanol.

Yield: 109.1 g (87.6%), purity >99% (GC)

Example 6: Preparation of Chloroacetaldehyde Dimethyl Acetal 200 ml of trichloromethane and 0.2 g of toluenesulfonic acid were placed in a 1 l four-neck flask provided with water separator, reflux condenser, precision glass stirrer and internal thermometer and metering unit. The mixture was heated to reflux on the water separator while stirring and, when reflux commenced, a mixture of 348.9 g of 45% strength aqueous chloroacetaldehyde solution (2 mol of chloroacetaldehyde), 96.12 g (3 mol) of methanol was metered in over a period of 6 hours. A further 96.12 g (3 mol) of methanol were then metered in over a period of 2 hours.

Yield: 209.6 g (84.1%), purity >99% (GC)

Example 7: Preparation of Chloroacetaldehyde Dimethyl Acetal 3140 g of 45% strength aqueous chloroacetaldehyde solution (18 mol of chloroacetaldehyde), 865 g (27 mol) of methanol, 1500 ml of trichloromethane and 3.6 g of p-toluenesulfonic acid were placed in a 6 l four-neck flask provided with water separator, reflux condenser, packed column, precision glass stirrer and internal thermometer and metering unit. The two-phase mixture was heated under reflux on the water separator while stirring. During the removal of water, a further 1153 g (36 mol) of methanol and 500 ml of trichloromethane were metered in, with the reaction mixture becoming a single phase. As soon as no more water was separated off, 40.14 g of tributylamine were added to effect neutralization and the reaction mixture was fractionally distilled under reduced pressure (80 mbar, 63° C.)

Yield 1900 g (88.8% of theory) purity >99% (GC)

What is claimed is:

1. A process for preparing a chloroacetaldehyde acetal of an aliphatic alcohol, wherein the chloroacetaldehyde acetal is obtained from an aqueous chloroacetaldehyde solution containing 30-50% by weight chloroacetaldehyde in a presence of the aliphatic alcohol to be acetalized and an acid catalyst by azeotropic removal of water with the aid of a solvent, wherein the solvent is trichloromethane.

2. The process as claimed in claim 1, wherein the aliphatic alcohol to be acetalized is a monohydric, dihydric or higher-functionality aliphatic alcohol having from one to twelve carbon atoms.

3. The process as claimed in claim 1, wherein the acid catalyst is a member selected from the group consisting of an inorganic acid, an organic acid and a strong acid ion exchange resin containing sulfonic acid groups.

4. The process as claimed in claim 1, wherein the acid catalyst is present in an amount of from 0.01 mol % to 2 mol % based on the chloroacetaldehyde used.

5. The process as claimed in claim 2, wherein the acid catalyst is a member selected from the group consisting of an inorganic acid, an organic acid and a strong acid ion exchange resin containing sulfonic acid groups.

6. The process as claimed in claim 5, wherein the acid catalyst is present in an amount of from 0.01 mol % to 2 mol % based on the chloroacetaldehyde used.

* * * * *